United States Patent
Nogami

(10) Patent No.: US 10,379,094 B2
(45) Date of Patent: Aug. 13, 2019

(54) CONTAMINATION CONTROL METHOD OF VAPOR DEPOSITION APPARATUS AND METHOD OF PRODUCING EPITAXIAL SILICON WAFER

(71) Applicant: SUMCO CORPORATION, Tokyo (JP)

(72) Inventor: Syouji Nogami, Tokyo (JP)

(73) Assignee: SUMCO CORPORATION, Tokyo (JP)

(*) Notice: Subject to any disclaimer, the term of this patent is extended or adjusted under 35 U.S.C. 154(b) by 356 days.

(21) Appl. No.: 14/857,198

(22) Filed: Sep. 17, 2015

(65) Prior Publication Data
US 2016/0097144 A1 Apr. 7, 2016

(30) Foreign Application Priority Data
Oct. 2, 2014 (JP) .................. 2014-204168

(51) Int. Cl.
*C30B 25/16* (2006.01)
*G01N 33/00* (2006.01)
(Continued)

(52) U.S. Cl.
CPC ..... *G01N 33/0004* (2013.01); *C23C 16/4405* (2013.01); *H01L 21/67253* (2013.01); *G01N 1/44* (2013.01); *H01L 21/0262* (2013.01); *H01L 21/02381* (2013.01); *H01L 21/02532* (2013.01); *H01L 22/12* (2013.01)

(58) Field of Classification Search
CPC ......... H01L 21/02381; H01L 21/02532; H01L 21/0262; H01L 21/67253; H01L 22/12; C30B 25/16
See application file for complete search history.

(56) References Cited

U.S. PATENT DOCUMENTS

2004/0175959 A1* 9/2004 Tamura .................. C30B 25/02
                                                           438/778
2009/0263971 A1 10/2009 Tanabe
(Continued)

FOREIGN PATENT DOCUMENTS

JP    H06-188198 A    7/1994
JP    06-260415 A     9/1994
(Continued)

*Primary Examiner* — Hua Qi
(74) *Attorney, Agent, or Firm* — Greenblum & Bernstein, P.L.C.

(57) ABSTRACT

A contamination control method includes: a wafer loading step for loading a monitor wafer in a chamber of a vapor deposition apparatus; a heat-treatment repetition step for consecutively repeating a heat-treatment step for thermally treating the monitor wafer for predetermined times; a wafer unloading step for unloading the monitor wafer from the chamber; and a wafer-contamination-evaluation step for evaluating a metal-contamination degree of the monitor wafer unloaded out of the chamber. The heat-treatment step includes a first heat-treatment step for thermally treating the monitor wafer in an atmosphere of a hydrogen-containing gas and a second heat-treatment step for thermally treating the monitor wafer in an atmosphere of a hydrogen-chloride-containing gas and the hydrogen-containing gas.

12 Claims, 5 Drawing Sheets

(51) Int. Cl.
  *H01L 21/67* (2006.01)
  *C23C 16/44* (2006.01)
  *G01N 1/44* (2006.01)
  *H01L 21/02* (2006.01)
  *H01L 21/66* (2006.01)

(56) References Cited

U.S. PATENT DOCUMENTS

| | | | |
|---|---|---|---|
| 2010/0229795 | A1* | 9/2010 | Tanabe ............... C23C 16/4404 118/725 |
| 2013/0145984 | A1* | 6/2013 | Zhang .................... C30B 25/02 117/97 |
| 2015/0243566 | A1* | 8/2015 | Arai ....................... H01L 22/12 438/14 |

FOREIGN PATENT DOCUMENTS

| | | | | |
|---|---|---|---|---|
| JP | H11-281542 | A | | 10/1999 |
| JP | 2003-309070 | A | | 10/2003 |
| JP | 2005-326219 | A | | 11/2005 |
| JP | 2010-171101 | A | | 8/2010 |
| JP | 2010-219494 | A | | 9/2010 |
| JP | 2010-239115 | A | | 10/2010 |
| JP | 2010272798 | A | * | 12/2010 |
| JP | 2012-174964 | A | | 9/2012 |
| JP | 2012-248692 | A | | 12/2012 |
| JP | 2012248692 | A | * | 12/2012 |
| JP | 2013-162026 | | | 8/2013 |
| JP | 2013-162092 | | | 8/2013 |
| JP | 2013-197364 | A | | 9/2013 |
| JP | 2014-082324 | | | 5/2014 |
| JP | 2014-099479 | A | | 5/2014 |
| JP | 2014-103328 | A | | 6/2014 |
| JP | 2014-165311 | A | | 9/2014 |
| JP | 2015-501533 | A | | 1/2015 |
| WO | WO-2013055368 | A1 | * | 4/2013 ............... G01N 1/32 |
| WO | WO-2014061413 | A1 | * | 4/2014 ............. H01L 22/12 |

* cited by examiner

CONTAMINATION CONTROL METHOD OF VAPOR DEPOSITION APPARATUS AND METHOD OF PRODUCING EPITAXIAL SILICON WAFER

The entire disclosure of Japanese Patent Application No. 2014-204168 filed on Oct. 2, 2014 is expressly incorporated by reference herein.

TECHNICAL FIELD

The present invention relates to a contamination control method of vapor deposition apparatus and a method of producing epitaxial silicon wafer.

BACKGROUND ART

In accordance with recent increase in resolution of camera function installed in digital cameras, smart phones, mobile PCs and the like, strengthening of contamination control of epitaxial silicon wafers to be used for image pickup devices such as CCD and CIS has come to be demanded.

Especially, pursuit of the cause for an occurrence of white defects, which are peculiar to image pickup devices, and process management therefor has been strongly requested. At present, it is speculated that the cause of the white defects is metal contamination. Especially, primary cause for the white defects is attributed to slowly diffusing metals such as Mo, W, Ti, Nb and Ta.

Examples of the source of the metal contamination in epitaxial silicon wafers include material gas used for growing epitaxial layer and cleaning gas for cleaning an interior of a chamber. Material of the chamber and a metal parts typically used for a pipe system are also the source of the metal contamination. Further, the source of the metal contamination also includes metal dusts issued from a parts (e.g. rotation unit) of an epitaxial growth apparatus.

In order to reduce contaminants caused from the epitaxial growth apparatus, the following evaluation methods have been proposed.

In a proposed method, steps including cleaning of a vapor deposition apparatus, loading of a silicon wafer, growth of an epitaxial layer and unloading of the silicon wafer are defined as one cycle, which is repeated for predetermined times to prepare a monitor wafer on which the epitaxial layer is grown for the predetermined times. Subsequently, the lifetime of the monitor wafer is measured to evaluate the cleanliness of the vapor deposition apparatus based on the lifetime value (see Patent Literature 1: JP-A-2013-162026).

In another example, a silicon wafer is subjected to a heat treatment after a target gas is introduced into a chamber in which the silicon wafer is disposed to expose the silicon wafer to the target gas, thereby diffusing metals having been contained in the target gas. Then, the lifetime of the monitor wafer after the heat treatment is measured to evaluate the metal contamination of the target gas based on the lifetime value (see Patent Literature 2: JP-A-2013-162092).

In still another example, after repeating for predetermined times a process for cleaning an interior of a chamber of a vapor deposition apparatus with vapor etching using HCl gas and heat treatment of a silicon wafer in a hydrogen atmosphere, contaminants on the surface of the silicon wafer is collected and the concentration of metal impurities contained in the contaminants is measured using ICP-MS (see Patent Literature 3: JP-A-2014-082324).

However, since the cycle is repeated for a plurality of times to provide the epitaxial layer in the above Patent Literature 1, detection sensitivity for the contaminant metal is inferior.

In Patent Literature 2, since the heat treatment is applied after exposing the silicon wafer to the target gas, the influence of the heat treatment cannot be separately evaluated.

Furthermore, since the cleaning step is included in the cycle in Patent Literatures 1 and 3, considerably long time is required for the entire treatment. In addition, since the cleaning step and the heat-treatment step are repeatedly conducted accompanying loading of the wafer into the chamber and unloading of the wafer out of the chamber, metal contaminant tends to be contained from a transfer system.

SUMMARY OF THE INVENTION

An object of the invention is to provide a contamination control method of a vapor deposition apparatus capable of detecting extremely minute amount of metal contaminant in a vapor deposition apparatus in detail, and a production method of an epitaxial silicon wafer.

A contamination control method of a vapor deposition apparatus according to an aspect of the invention includes: loading a monitor wafer into an interior of a chamber of a vapor deposition apparatus; consecutively repeating a heat treatment for thermally treating the monitor wafer loaded into the interior of the chamber for predetermined number of times; unloading the monitor wafer after experiencing the repetition of the heat treatment from the interior of the chamber; and evaluating a metal-contamination degree of the monitor wafer unloaded out of the chamber, in which the heat treatment comprises: a first heat-treatment, in which a hydrogen-chloride-containing gas is not fed into the interior of the chamber but a hydrogen-containing gas is fed into the chamber to thermally treat the monitor wafer in an atmosphere of the hydrogen-containing gas; and a second heat-treatment, in which the hydrogen-chloride-containing gas and the hydrogen-containing gas are fed into the interior of the chamber to thermally treat the monitor wafer in an atmosphere of the hydrogen-chloride-containing gas and the hydrogen-containing gas.

According to the above aspect of the invention, since the heat treatment (the first heat-treatment) is conducted in the atmosphere of the hydrogen-containing gas, the metal present in the chamber is reduced by the hydrogen-containing gas. Accordingly, even when metal is present in a form of an easily vaporizable compound, the metal compound is reduced in the first heat treatment to be kept from being vaporized. For instance, Mo and W react with oxygen to be vaporized in a form of an oxide when being adhered to a wafer under a high temperature. However, Mo and W are not vaporized from the surface of the wafer in the above reductive atmosphere. Consequently, the vaporized amount of metal is decreased, thereby allowing efficient accumulation of the metal to the monitor wafer.

Further, since the monitor wafer is exposed to the hydrogen-containing gas at a high temperature in the first heat-treatment, a natural oxide film present on the surface of the monitor wafer is removed. Accordingly, the surface of the monitor wafer is always kept in a state to be easily contaminated by metal in the first heat-treatment, so that the metal is efficiently accumulated therein.

Further, the second heat-treatment is applied under the atmosphere of the hydrogen-chloride-containing gas and the hydrogen-containing gas. An uppermost layer of the surface of the monitor wafer is etched with hydrogen chloride by experiencing the second heat-treatment, whereby the surface of the monitor wafer is cleaned. The cleaned surface of the monitor wafer becomes active. The surface of the monitor wafer having thus experienced the second heat-treatment becomes activate (i.e. for the metal to be easily adsorbed), so that the metal is efficiently adsorbed to the surface of the monitor wafer.

Then, the first heat-treatment is consecutively repeated, so that the metal adsorbed on the surface is dispersed in the monitor wafer. As a result, the metal is efficiently accumulated in the monitor wafer.

Further, since the hydrogen-chloride-containing gas is fed in the second heat-treatment, the metal contamination derived from a pipe system for supplying the hydrogen-chloride-containing gas can be more efficiently evaluated.

In the repeating of the heat treatments (heat-treatment repetition step), the heat-treatments including the first heat treatment and the second heat treatment are consecutively repeated for predetermined times. The heat treatments are repeatedly conducted in the heat-treatment repetition step, thereby repeatedly exposing the monitor wafer to an environment contaminated with metal. Thus, the metal is accumulated in the monitor wafer to a level capable of being reliably detected in the wafer contamination evaluation. As a result, extremely minute amount of metal contamination of Mo, W, Ti, Nb, Ta and the like can be measured. Based on the measured metal concentration, the contamination in the vapor deposition apparatus can be controlled.

Further, the heat-treatment repetition step is only required in order to emphasize the contamination, where no loading/unloading of the monitor wafer into/out of the chamber is required each time the heat treatment is repeated. Consequently, metal does not transfer to the outside of the chamber in accordance with the open/close operation of the chamber, thereby allowing efficient accumulation of the metal to the monitor wafer. Further, the contamination derived from the delivery system can be restrained to the minimum.

In the contamination control method of a vapor deposition apparatus according to the above aspect of the invention, a heat treatment temperature of the second heat-treatment is preferably in a range of a heat treatment temperature in the first heat-treatment ±100 degrees C.

According to the above arrangement, the heat treatment temperature of the second heat treatment is in a range of the heat treatment temperature in the first heat treatment ±100 degrees C. With the above heat treatment temperature in the second heat treatment, the surface of the monitor wafer can be efficiently cleaned.

In the contamination control method of a vapor deposition apparatus according to the above aspect of the invention, a treatment time of the second heat treatment is preferably in a range from 1 to 200 seconds.

According to the above arrangement, the treatment time of the second heat treatment is in a range from 1 to 200 seconds. With the above treatment time in the second heat treatment, the surface of the monitor wafer can be efficiently cleaned.

In the contamination control method of a vapor deposition apparatus according to the above aspect of the invention, a supply flow rate of the hydrogen-chloride-containing gas in the second heat-treatment is preferably in a range from 0.1 slm to 5.0 slm.

According to the above arrangement, the supply flow rate of the hydrogen-chloride-containing gas in the second heat treatment is in a range from 0.1 slm to 5.0 slm. With the above supply flow rate of the hydrogen-chloride-containing gas, the surface of the monitor wafer can be efficiently cleaned.

In the contamination control method of a vapor deposition apparatus according to the above aspect of the invention, a heat treatment temperature in the first heat-treatment is preferably in a range from 900 to 1200 degrees C.

According to the above arrangement, the heat treatment temperature in the first heat treatment is in a range from 900 to 1200 degrees C. With the above heat treatment temperature in the first heat treatment, the metal is efficiently accumulated on the surface of the monitor wafer. Further, the above heat treatment temperature range is overlapped with the heat treatment temperature range for growing epitaxial layer. Accordingly, the heat treatment of the present exemplary embodiment can be performed without changing the heat treatment temperature conditions for growing epitaxial layer.

In the contamination control method of a vapor deposition apparatus according to the above aspect of the invention, a repetition number of the repetition of the heat-treatment steps is preferably in a range from 2 to 20.

According to the above arrangement, the repetition number of the heat treatments in the heat-treatment repetition step is in a range from 2 to 20. With the repetition number of the heat-treatment step defined in the above range, the monitor wafer with the metal being accumulated therein to a concentration detectable in the wafer-contamination-evaluation step can be prepared. As a result, extremely minute amount of metal contamination of Mo, W, Ti, Nb, Ta and the like can be measured. Based on the measured metal concentration, the contamination in the vapor deposition apparatus can be controlled.

In the contamination control method of a vapor deposition apparatus according to the above aspect of the invention, prior to loading the monitor wafer into the chamber, a vapor-phase etching is preferably applied to the interior of the chamber using the hydrogen-chloride-containing gas to clean the interior of the chamber.

According to the above arrangement, prior to loading the wafer into the chamber, the cleaning for applying a vapor-phase etching to the interior of the chamber using the hydrogen-chloride-containing gas to clean the interior of the chamber is performed. Through the cleaning, the deposits deposited inside the chamber during the epitaxial-layer growth process can be appropriately removed.

It should be noted that the cleaning is only required before the monitor wafer is loaded into the chamber and is not necessary to be repeatedly conducted. Accordingly, the entire treatment time can be shortened.

In the contamination control method of a vapor deposition apparatus according to the above aspect of the invention, after cleaning the chamber, temperatures of the susceptor inside the chamber are preferably raised to a predetermined temperature range, and circulating a silane-containing gas in the chamber to form a polysilicon film on the surface of the susceptor.

According to the above arrangement, the coating is conducted after the deposits deposited inside the chamber during the epitaxial-layer growth process is removed through the cleaning. The susceptor tends to contain a large amount of metal impurities and thus is likely to be a contamination source. By conducting the coating step, the surface of the susceptor is coated with the polysilicon film to avoid the metal contamination derived from the susceptor.

Since the influence of the metal contamination from the susceptor can be removed, clearer evaluation results can be obtained.

In the contamination control method of a vapor deposition apparatus according to the above aspect of the invention, the evaluation of the wafer contamination is preferably performed based on a metal concentration measurement by a chemical analysis and/or a lifetime measurement.

According to the above arrangement, the wafer contamination evaluation is performed based on metal concentration measurement by chemical analysis and/or lifetime measurement. In the metal concentration measurement by the chemical analysis, the concentration of each of the metal elements at the surface layer can be detected. Accordingly, the metal contamination status of the vapor deposition apparatus can be recognized in detail, so that adequate control can be conducted. Further, though the lifetime measurement cannot determine what kind of and how much metal is contained, the lifetime measurement is advantageous in that the entirety of the wafer is subjected to the measurement and the measurement process is simple. Accordingly, the metal contamination in the vapor deposition apparatus is easily recognizable. These measurement processes are separately usable depending on the evaluation item of the wafer contamination, or both of the measurement processes may be used in combination.

In the contamination control method of a vapor deposition apparatus according to the above aspect of the invention, the chemical analysis is preferably performed using an induction coupled plasma mass spectrometry.

Alternatively, in the contamination control method of a vapor deposition apparatus according to the above aspect of the invention, the chemical analysis is preferably performed using a vapor-phase decomposition.

According to the above arrangements, since the plasma mass spectrometry or the vapor-phase decomposition is used for the chemical analysis, the concentration of the metal elements contained to the surface and in the surface layer of the contamination-emphasized monitor wafer can be easily measured.

A production method of an epitaxial silicon wafer according to another aspect of the invention includes: producing an epitaxial silicon wafer using a vapor deposition apparatus that is controlled by the contamination control method of a vapor deposition apparatus according to the above aspect of the invention.

According to the above aspect of the invention, since the epitaxial silicon wafer is produced using the vapor deposition apparatus of which metal contamination is controlled using the above contamination control method, an epitaxial silicon wafer of which metal contamination is controlled within a predetermined metal concentration can be obtained.

BRIEF DESCRIPTION OF DRAWING(S)

FIG. 1 schematically shows a vapor deposition apparatus (contamination control target) according to the invention.

DESCRIPTION OF EMBODIMENT(S)

First Exemplary Embodiment

Exemplary embodiment(s) of the invention will be described below with reference to the attached drawings.

Arrangement of Vapor Deposition Apparatus

An exemplary vapor deposition apparatus to be a contamination control target of a first exemplary embodiment is a single-wafer vapor deposition apparatus in which an epitaxial layer is vapor-deposited on a surface of a silicon wafer.

Figure 1:
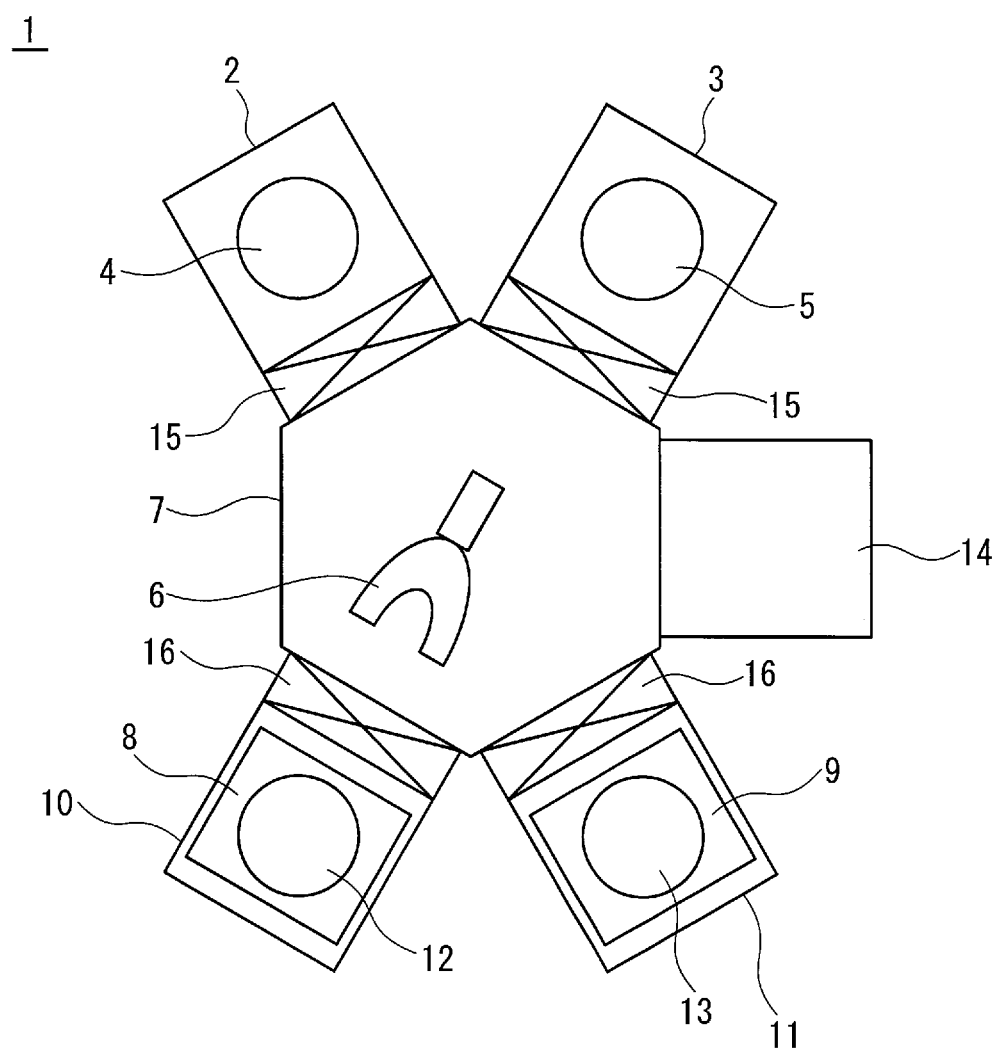

As shown in FIG. 1, a vapor deposition apparatus 1 includes a transfer chamber 7, and vapor deposition chambers 2, 3, load lock chambers 10, 11 and a cooling chamber 14, which are connected with and arranged around the transfer chamber 7. A wafer transfer device 6 is disposed in the transfer chamber 7. The silicon wafer is loaded into and unloaded out of each of the chambers using the wafer transfer device 6. Susceptors 4, 5 are respectively disposed in the chamber 2, 3. Cassettes 8, 9 capable of respectively receiving silicon wafers 12, 13 are respectively disposed in the load lock chambers 10, 11. It should be noted that the cooling chamber 14 is used for cooling the silicon wafers 12, 13. Openable/closable gate valves 15, 16 are respectively provided between the transfer chamber 7 and the chambers 2, 3 and between the transfer chamber 7 and the load lock chambers 10, 11.

Manufacture of Epitaxial Silicon Wafer Using Vapor Deposition Apparatus

Next, a process for producing an epitaxial silicon wafer using the vapor deposition apparatus 1 as arranged above will be described below.

Initially, the silicon wafers 12, 13 to be subjected to vapor deposition process are loaded to the cassettes 8, 9 disposed in the load lock chambers 10, 11. Then, the load lock chambers 10, 11 are hermetically sealed and the interiors of the load lock chambers 10, 11 are decompressed by vacuuming using a vacuum pump and the like. Subsequently, inactive gas (e.g. nitrogen gas) is introduced into each of the load lock chambers 10, 11 to purge the atmosphere inside the load lock chambers 10, 11 with the inactive gas.

After the atmosphere is purged with the inactive gas, the gate valve 16 is opened and the silicon wafer 12, 13 are unloaded out of the load lock chambers 10, 11 using the wafer transfer device 6.

Subsequently, the unloaded silicon wafers 12, 13 are loaded into the chambers 2, 3 having been purged with hydrogen-gas atmosphere, and the silicon wafers 12, 13 are mounted on the susceptors 4, 5. A loading temperature at which the silicon wafers 12, 13 are loaded into the chambers 2, 3 is, for instance, preferably in a range from 550 to 800 degrees C.

Then, the gate valves 15 are closed and interiors of the chambers 2, 3 are heated to a hydrogen-heat-treatment temperature. The hydrogen-heat-treatment temperature is preferably in a range from 1050 to 1200 degrees C. Subsequently, the silicon wafers 12, 13 are heated to a desired growth temperature and source gas and carrier gas are fed substantially horizontally to the surfaces of the silicon wafers 12, 13. The growth temperature is preferably in a range from 950 to 1180 degrees C. The source gas is preferably silane gas such as TCS (trichlorosilane: SiHCl3), $SiH_2Cl_2$ and $SiCl_4$. The carrier gas is preferably hydrogen gas. With a treatment for a predetermined time under the above-described conditions, the epitaxial layer with a desired thickness is vapor-deposited on the surfaces of the silicon wafers 12, 13 to produce epitaxial silicon wafers.

Subsequently, the produced epitaxial silicon wafers are unloaded out of the chambers 2, 3 using the wafer transfer device 6. Then, after being cooled inside the cooling chamber 14, the epitaxial silicon wafers are transferred to the cassettes 8, 9 disposed inside the load lock chambers 10, 11. Further, the epitaxial silicon wafers are unloaded out of the vapor deposition apparatus 1 together with the cassettes 8, 9.

Through the above-described epitaxial-layer-growth process, by-products from the source gas are deposited inside the chambers 2, 3. The presence of the deposits may decrease the quality of the produced epitaxial silicon wafer (e.g. adhesion of particles on the epitaxial silicon wafer). Accordingly, the deposits have to be regularly removed.

Figure 2:
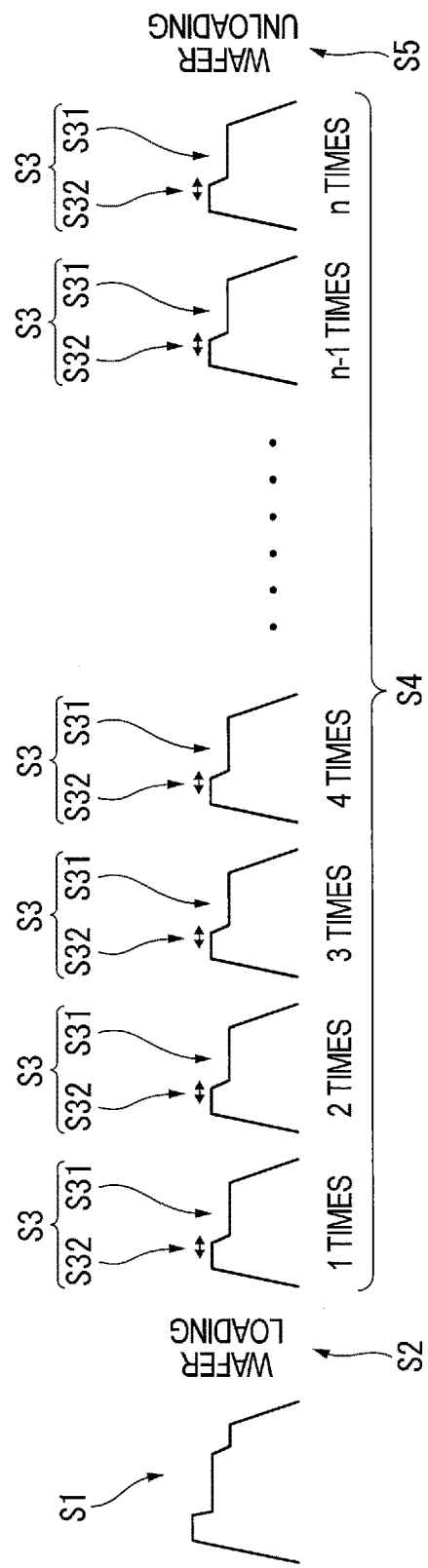
FIG. 2 shows process steps of a contamination control method for the vapor deposition apparatus according to the invention.

As shown in FIG. 2, a contamination control method of a vapor deposition apparatus according to the present exemplary embodiment includes a cleaning step S1, a wafer loading step S2, a heat-treatment repetition step S4 in which a heat-treatment step S3 including a first heat-treatment step S31 and a second heat-treatment step S32 are consecutively repeated for predetermined number of times, a wafer unloading step S5, and a wafer-contamination-evaluation step.

The above steps will be detailed below.

Cleaning Step S1

In the contamination control method according to the first exemplary embodiment, the interior of the chambers 2, 3 of the vapor deposition apparatus 1 after experiencing the above-described epitaxial-layer growth process is cleaned (cleaning step S1). In the cleaning step S1, the interior of each of the chambers 2, 3 is heated to a predetermined temperature and a hydrogen-chloride-containing gas is circulated therein. Through the above process, the deposits deposited inside the chambers 2, 3 during the epitaxial-layer growth step is etched. The cleaning step is preferably conducted under the conditions of heating the interior of the chamber in a range from 900 to 1200 degrees C. and circulating the hydrogen-chloride-containing gas for 10 to 300 seconds.

The above temperature range is defined because the contamination is not sufficiently caused inside the chambers 2, 3 at a temperature lower than 900 degrees C., and the heating performance and heat resistance of the chambers 2, 3 are not sufficient at a temperature higher than 1200 degrees C. Further, the above range of the cleaning time is defined because the contamination is not sufficiently caused by the hydrogen-chloride-containing gas when the cleaning time is less than 10 seconds and the treatment time is excessively long when the cleaning time exceeds 300 seconds.

Wafer Loading Step S2

Subsequently, hydrogen gas is circulated inside the cleaned chambers 2, 3 to purge the atmosphere inside the chambers 2, 3 with the hydrogen-gas, and then the monitor wafer is loaded onto the susceptors 4, 5 in the chambers 2, 3, in which temperature has been adjusted to a loading temperature (e.g. 650 degrees C.). In the first exemplary embodiment hereinafter, the silicon wafers 12, 13 will be referred to as the monitor wafer for the convenience of explanation.

Heat-Treatment Repetition Step S4

In the heat-treatment repetition step S4, the heat-treatment step S3 is consecutively repeated for predetermined times.

The repetition number of the heat-treatment step S3 is preferably in a range from 2 to 20, more preferably in a range from 2 to 10, especially preferably in a range from 5 to 10. When the repetition number of the above heat-treatment step S3 is less than the lower limit, metal is not sufficiently accumulated in the monitor wafer, so that metal concentration may not be detected during the wafer-contamination-evaluation step (described below). On the other hand, the repetition number of the heat-treatment step S3 exceeding the upper limit is inefficient because no significant change in effects can be found.

Heat-Treatment Step S3

The heat-treatment step S3 includes the first heat-treatment step S31 and the second heat-treatment step S32. In the second heat-treatment step S32, hydrogen-chloride-containing gas is additionally fed during the first heat-treatment step S31.

First Heat-Treatment Step S31

In the first heat-treatment step S31, hydrogen-chloride-containing gas is not fed into the chambers 2, 3 but hydrogen-containing gas is fed therein to subject the monitor wafer to a heat treatment in an atmosphere of hydrogen-containing gas.

The heat treatment temperature in the first heat-treatment step S31 is preferably in a range from 900 to 1200 degrees C., more preferably 1050 to 1200 degrees C. Further, it is preferable that the hydrogen-containing gas is circulated for 10 to 300 seconds.

The above temperature range for the heat treatment temperature is defined because the contamination is not sufficiently caused inside the chambers 2, 3 at a temperature lower than 900 degrees C., and the heating performance and heat resistance of the chambers 2, 3 are not sufficient at a temperature higher than 1200 degrees C. Further, the above range of the heat treatment time is defined because the contamination may not be sufficiently collected when the heat treatment time is less than 10 seconds and the treatment time is excessively long when the heat treatment time exceeds 300 seconds.

Second Heat-Treatment Step S32

In the second heat-treatment step S32, the hydrogen-chloride-containing gas and the hydrogen-containing gas are fed into the chambers 2, 3 to subject the monitor wafer to a heat treatment in an atmosphere of the hydrogen-chloride-containing gas and the hydrogen-containing gas. An uppermost layer of the surface of the monitor wafer is etched by experiencing the second heat-treatment step, whereby the surface of the monitor wafer is cleaned. The cleaned surface of the monitor wafer becomes active. The surface of the monitor wafer having thus experienced the second heat-treatment step to be activated becomes easily contaminated by metal, so that the metal is efficiently accumulated therein.

Further, since the hydrogen-chloride-containing gas is fed in the second heat-treatment step, the metal contamination derived from a pipe system for supplying the hydrogen-chloride-containing gas can be more efficiently evaluated.

The heat treatment temperature in the second heat-treatment step S32 is preferably in a range of (heat treatment temperature in the first heat-treatment step S31 (first heat treatment temperature) ±100 degrees C., more preferably in a range of the first heat treatment temperature ±50 degrees C., especially preferably in a range of the first heat treatment temperature ±25 degrees C.

When the heat treatment temperature in the second heat-treatment step S32 is lower than the above range, the metal contamination may not be sufficiently introduced into the monitor wafer, so that the detection sensitivity may be decreased. On the other hand, when the heat treatment temperature is higher than the above range, the surface of the monitor wafer may be excessively etched. In this case, the metal contamination already introduced onto the surface of the monitor wafer may be removed by the etching.

The treatment time of the second heat-treatment step S32 is preferably in a range from 1 to 200 seconds, more preferably 10 to 60 seconds, especially preferably 15 seconds. When the treatment time in the second heat-treatment step is less than the above range, the metal contamination may not be sufficiently emphasized even after applying the second heat-treatment step S32. On the other hand, when the treatment time is longer than the above range, the entire treatment time may be lengthened.

The supply flow rate of the hydrogen-chloride-containing gas in the second heat-treatment step S32 is preferably in a range from 0.1 slm to 5.0 slm, more preferably in a range from 0.2 slm to 2.0 slm, especially preferably in a range from 0.5 slm to 1.0 slm. When the supply flow rate of the hydrogen-chloride-containing gas falls below the above range, the metal contamination from the pipe system for supplying the hydrogen-chloride-containing gas may not be sufficiently introduced. On the other hand, when the supply flow rate is higher than the above range, the surface of the monitor wafer may be excessively etched. In this case, the metal contamination already introduced onto the surface of the monitor wafer may be removed by the etching.

Wafer Unloading Step S5

Next, the monitor wafer having experienced the heat-treatment repetition step S4 is unloaded out of the chambers 2, 3 into the transfer chamber 7. The monitor wafer of which metal contamination is emphasized in the heat-treatment repetition step S4 is unloaded out of the chambers 2, 3 using the wafer transfer device 6 and, after being cooled in the cooling chamber 14, transferred out of the vapor deposition apparatus 1.

Wafer-Contamination-Evaluation Step

Next, a metal-contamination degree of the monitor wafer having been unloaded out of the chambers 2, 3 in the wafer unloading step S5 is evaluated. The evaluation of wafer contamination is preferably performed based on metal concentration measurement by chemical analysis and/or lifetime measurement.

Chemical Analysis

The monitor wafer of which metal contamination is emphasized is subjected to a chemical analysis to measure the metal concentration in the monitor wafer. In the metal concentration measurement by the chemical analysis, the concentration of each of the metal elements at the surface layer can be detected. Accordingly, the contamination in the chambers 2, 3 of the vapor deposition apparatus 1 can be recognized for each of the metal elements in detail based on the metal concentration measured by the chemical analysis.

The target of the analysis of the contamination control method according to the first exemplary embodiment is a metal with a low diffusion rate such as Mo, W, Ti, Nb, and Ta. In addition to the above low-diffusion-rate metals, Cr, Fe, Ni, and Cu may be the target of the analysis. In the first exemplary embodiment, it is preferable that the chemical analysis is performed using an induction coupled plasma mass spectrometry. Alternatively, it is also preferable that the chemical analysis is performed using a vapor-phase decomposition.

Since the metal subjected to the analysis (i.e. Mo, W, Ti, Nb, or Ta) is low in diffusion rate, it is speculated that the most of metal is present on the surface of the monitor wafer and in a surface layer at a depth of approximately 5 μm. Accordingly, the metal contamination can be controlled by analyzing the surface and the surface layer of the monitor wafer of which metal contamination is emphasized.

Lifetime Measurement

The lifetime can be obtained by measuring a recombination time (recombination lifetime) of carriers (holes and electrons) of the monitor wafer of which metal contamination is emphasized, using, for instance, g-PCD method. When there is heavy metal contamination in the monitor wafer, the recombination lifetime is shortened. Accordingly, the quality of the monitor wafer can be easily determined by measuring the recombination lifetime.

Production Method of Epitaxial Silicon Wafer

In the production method of an epitaxial silicon wafer according to the first exemplary embodiment, the epitaxial silicon wafer is produced using the vapor deposition apparatus 1 that is controlled according to the above contamination control method.

Since the vapor deposition apparatus 1, of which contamination in the chambers 2, 3 is detected for each of the metal elements using the above contamination control method, is used, an epitaxial silicon wafer that is controlled to have a metal concentration in a predetermined range can be obtained.

Advantage(s) of Exemplary Embodiment

The first exemplary embodiment as described above provides the following advantages.

(1) In the first heat-treatment step, the heat treatment is applied under the hydrogen-containing gas atmosphere. Accordingly, even when metal is present in a form of an easily vaporizable compound, the metal compound is reduced by the hydrogen-containing gas to be kept from being vaporized. Consequently, the vaporized amount of metal is reduced, thereby allowing efficient accumulation of the metal to the monitor wafer.

(2) Since the monitor wafer is exposed to the hydrogen-containing gas at a high temperature in the first heat-treatment step, the natural oxide film present on the surface of the monitor wafer is removed. Accordingly, the surface of the monitor wafer is always kept to be easily contaminated by metal in the first heat-treatment step, so that the metal is efficiently accumulated in the monitor wafer.

(3) In the second heat-treatment step, the heat treatment is applied under the atmosphere of the hydrogen-chloride-containing gas and the hydrogen-containing gas. Accordingly, the uppermost layer of the surface of the monitor wafer is etched by hydrogen chloride, whereby the surface of the monitor wafer is cleaned to be activated. Since the surface of the monitor wafer thus becomes easily contaminated by metal, so that the metal is efficiently adsorbed to the surface of the monitor wafer. Then, the first heat-treatment step is consecutively repeated, so that the metal adsorbed on the surface is dispersed in the monitor wafer. As a result, the metal is efficiently accumulated in the monitor wafer.

Further, since the hydrogen-chloride-containing gas is fed in the second heat-treatment step, the metal contamination derived from a pipe system for supplying the hydrogen-chloride-containing gas can be more efficiently evaluated.

(4) In the heat-treatment repetition step, the heat-treatment step including the first heat-treatment step and the second heat-treatment step is consecutively repeated for predetermined times. Accordingly, the monitor wafer is repeatedly exposed to an environment contaminated with metal. Thus, the metal is accumulated in the monitor wafer to a level reliably detectable in the wafer-contamination-evaluation step. As a result, an extremely minute amount of metal contamination of Mo, W, Ti, Nb, Ta and the like can be measured. Based on the measured metal concentration, the contamination in the vapor deposition apparatus can be controlled.

(5) The repetition number of the heat-treatment steps in the heat-treatment repetition step is in a range from 2 to 20. With the repetition number of the heat-treatment step defined in the above range, the monitor wafer, in which metal is accumulated to a concentration detectable in the wafer-contamination-evaluation step, can be prepared.

(6) The heat treatment temperature in the first heat-treatment step is in a range from 900 to 1200 degrees C. With the above heat treatment temperature, the metal is efficiently accumulated in the monitor wafer. Further, the above heat treatment temperature range is overlapped with the heat treatment temperature range for growing epitaxial layer. Accordingly, the heat-treatment step of the present exemplary embodiment can be performed without changing the heat treatment temperature conditions for growing epitaxial layer.

(7) The heat treatment temperature of the second heat-treatment step is in a range of the first heat treatment temperature ±100 degrees C. With the above heat treatment temperature in the second heat-treatment step, the surface of the monitor wafer can be efficiently cleaned.

(8) The treatment time of the second heat-treatment step is in a range from 1 second to 200 seconds. With the above treatment time in the second heat-treatment step, the surface of the monitor wafer can be efficiently cleaned.

(9) The supply flow rate of the hydrogen-chloride-containing gas in the second heat-treatment step is in a range from 0.1 slm to 5.0 slm. With the above supply flow rate of the hydrogen-chloride-containing gas, the surface of the monitor wafer can be efficiently cleaned.

(10) Prior to the wafer loading step, the cleaning step for applying a vapor-phase etching to the interior of the chamber using the hydrogen-chloride-containing gas to clean the interior of the chamber is performed. Through the cleaning step, the deposits deposited inside the chamber during the epitaxial-layer growth process can be appropriately removed.

(11) The wafer-contamination-evaluation step is performed based on the metal concentration measurement by the chemical analysis and/or the lifetime measurement. In the metal concentration measurement by the chemical analysis, the concentration of each of the metal elements at the surface layer can be detected. Accordingly, the metal contamination status of the vapor deposition apparatus 1 can be recognized in detail, so that further detailed control can be conducted. Further, though the lifetime measurement cannot determine what kind of and how much metal is contained, the lifetime measurement is advantageous in that the measurement target is the entirety of the wafer and the measurement process is simple. Accordingly, the metal contamination in the vapor deposition apparatus is easily recognizable. These measurement processes are usable depending on the evaluation item of the wafer contamination, or both of the measurement processes may be used in combination.

(12) The induction coupled plasma mass spectrometry or the vapor-phase decomposition is used for the chemical analysis. Accordingly, the concentration of the metal elements contained on the surface and in the surface layer of the contamination-emphasized monitor wafer, can be easily measured.

Modification(s)

It should be understood that the scope of the invention is not limited to the above-described exemplary embodiment, but includes various improvement(s) and modification(s) of design as long as such improvement(s) and modification(s) are compatible with the invention.

Though the metal concentration on the surface and in the surface layer of the monitor wafer is measured using a chemical analysis in the first exemplary embodiment, a bulk analysis may be performed on the monitor wafer.

In the heat-treatment repetition step, the monitor wafer may be loaded into and unloaded out of the chamber each time a single heat-treatment step is performed.

Specific process and structures may be altered in implementing the invention as long as an object of the invention is achievable.

Second Exemplary Embodiment

Next, a second exemplary embodiment of the invention will be described below.

The vapor deposition apparatus (contamination control target) in the second exemplary embodiment is the same as the vapor deposition apparatus 1 in the first exemplary embodiment shown in FIG. 1. Accordingly, the arrangement of the vapor deposition apparatus of the second exemplary embodiment will not be described.

In the second exemplary embodiment, a coating step is applied subsequent to the cleaning step S1. In the coating step, the temperatures of the susceptors 4, 5 inside the chambers 2, 3 are raised to a predetermined temperature range, and silane-containing gas is circulated in the chambers 2, 3 to form a polysilicon film on the surface of the susceptors 4, 5.

By conducting the coating step, the surface of the susceptors 4, 5 after being cleaned is coated with the polysilicon film to avoid the metal contamination derived from the susceptors 4, 5. Since the influence of the metal contamination from the susceptors 4, 5 can be removed, clearer evaluation results can be obtained.

EXAMPLES

Next, the invention will be described in further detail below with reference to Examples and Comparatives. However, the scope of the invention is by no means limited by these Examples and Comparatives.

Example 1

An n-type silicon wafer having 300 mm diameter was used as the monitor wafer. An epitaxial growth apparatus capable of producing an epitaxial silicon wafer for image pickup devices was used as a vapor deposition apparatus. Then, various treatments were applied according to the following conditions to prepare monitor wafers in which metal contamination was emphasized (metal-contamination-emphasized monitor wafer).

Metal-contamination-emphasized monitor wafer(s) was prepared through a cleaning step, wafer loading step, heat-treatment repetition step, and wafer unloading step. The repetition number of the heat-treatment steps in the heat-treatment repetition step was five. The treatment conditions in the cleaning step were HCL gas atmosphere, heat treatment temperature of 1120 degrees C., and treatment time of 75 seconds. The treatment conditions in the first heat-treatment step were hydrogen gas atmosphere, heat treatment temperature of 1120 degrees C., and treatment time of 270 seconds. The treatment conditions in the second heat-treatment step were HCL gas and hydrogen gas atmosphere, heat treatment temperature of 1150 degrees C., treatment time of 15 seconds, and HCL supply flow rate of 0.75 slm.

Example 2

Except that the repetition number of the heat-treatment step in the heat-treatment repetition step was changed to 10, metal-contamination-emphasized monitor wafer(s) was prepared in the same manner as the above Example 1.

Comparative 1

An n-type silicon wafer having 300 mm diameter similar to that in the above Example 1 was prepared as a monitor wafer and the same epitaxial growth apparatus was used. Then, various treatments were applied according to the following conditions to produce monitor wafers in which metal contamination was emphasized.

Metal-contamination-emphasized monitor wafer(s) was prepared through a cleaning step, wafer loading step, heat-treatment step, and wafer unloading step. A repetition number of a cycle of the cleaning step, wafer loading step, heat-treatment step, and wafer unloading step was five. The treatment conditions in the cleaning step were HCL gas atmosphere, heat treatment temperature of 1120 degrees C., and treatment time of 75 seconds. The treatment conditions in the heat-treatment step were hydrogen gas atmosphere, heat treatment temperature of 1120 degrees C., and treatment time 270 seconds.

Reference Example 1

The same n-type silicon wafer having 300 mm diameter as that in the above Example 1 was prepared as a monitor wafer and the same epitaxial growth apparatus was used. Then, various treatments were applied according to the following conditions.

A cleaning step, wafer loading step, epitaxial-layer growth step, and wafer unloading step were conducted on a monitor wafer.

The treatment conditions in the cleaning step were HCL gas atmosphere, heat treatment temperature of 1120 degrees C., and treatment time of 75 seconds. The treatment conditions in the epitaxial-layer growth step were hydrogen gas and TCS gas atmosphere, heat treatment temperature of 1120 degrees C., and treatment time of 270 seconds.

Wafer Contamination Evaluation 1

Figure 3:
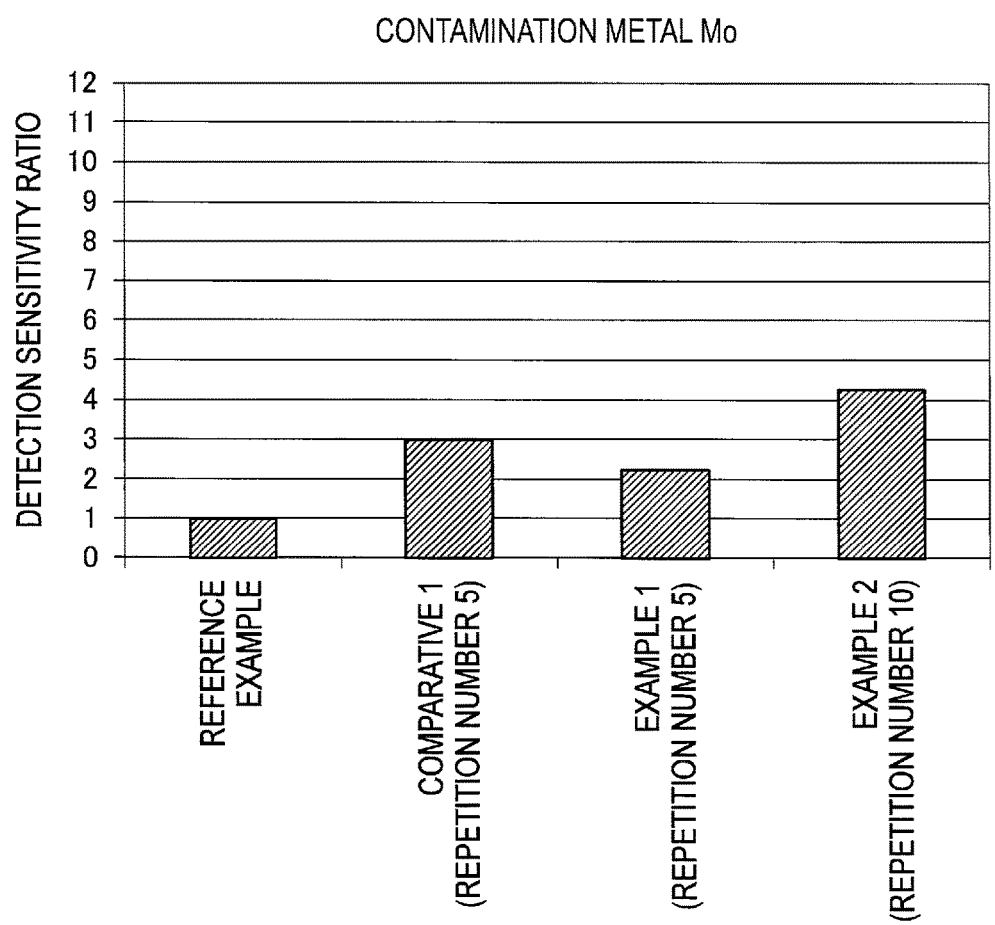
FIG. 3 is a graph showing a detection sensitivity ratio of Mo concentration in Examples 1 and 2 and Comparative 1.
Figure 4:
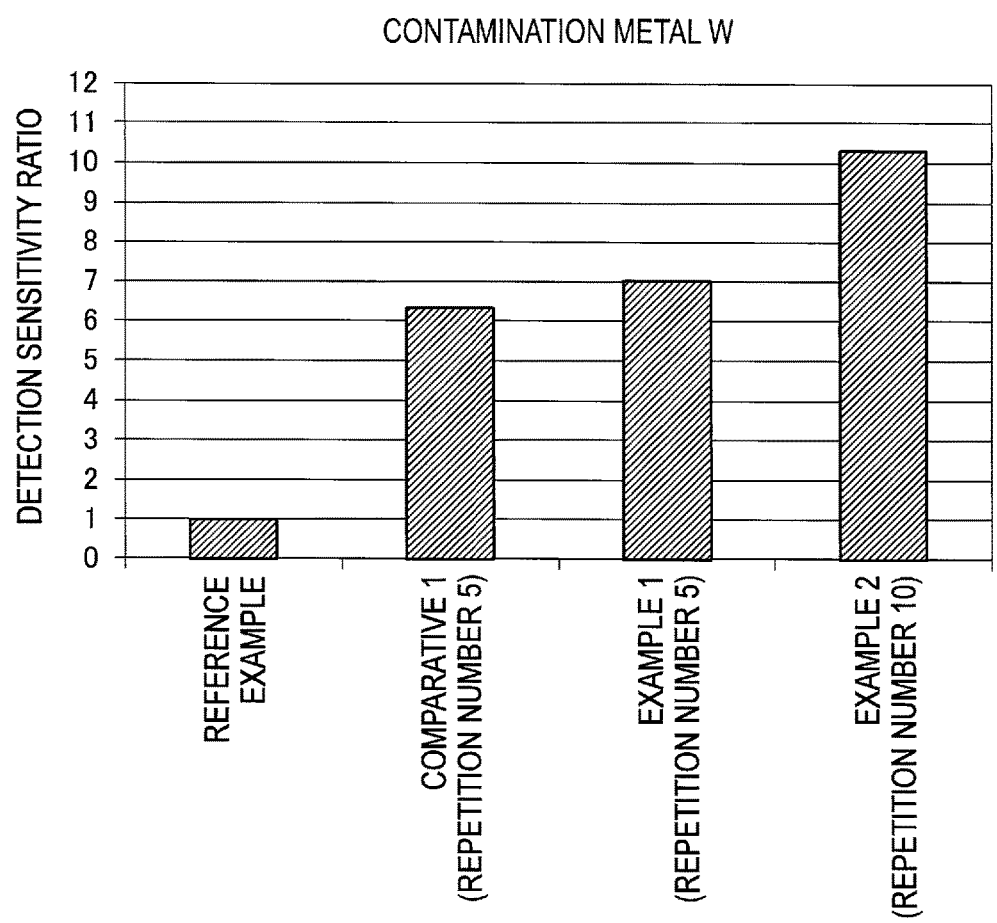
FIG. 4 is a graph showing a detection sensitivity ratio of W concentration in Examples 1 and 2 and Comparative 1.

The following surface analysis was conducted on the monitor wafers having experienced the various treatments described in Examples 1 and 2, Comparative 1 and Reference Example 1 to measure a metal concentration of W and Mo. FIGS. 3 and 4 show the results. It should be noted that a detection sensitivity ratio represented by each of ordinate axes in FIGS. 3 and 4 show a relative value where a detection sensitivity of the Reference Example (without contamination emphasizing) is defined as 1.

Surface Analysis

A mixture solution of hydrofluoric acid and hydrogen peroxide water was brought into contact with the surface of the monitor wafer after experiencing the various treatments, thereby collecting the metal present on the surface of the monitor wafer. The collected metal was measured using induction coupled plasma mass spectrometry to calculate the concentration of each of the metal elements on the surface of the monitor wafer.

As shown in FIGS. 3 and 4, Examples 1, 2 and Comparative 2 exhibit higher detection sensitivity than that in the Reference Example, whereby it is confirmed that the metal contamination is emphasized.

As shown in FIG. 3, with the same repetition number (i.e. five), the detection sensitivity in Example 1 was slightly inferior to Comparative 1 in detecting Mo. On the other hand, the treatment time in Example 1 is reduced to approximately half of that in Comparative 1, and it is found that the contamination state can be easily recognized by the contamination control method of the invention in detecting Mo.

Further, Example 2 with the repetition number of ten showed higher detection sensitivity than that in Comparative 1. Though Example 2 had more repetition number than that in Comparative 1, considering that Comparative 1 includes the cleaning step in one cycle and thus the wafer has to be loaded into and out of the chamber, it is found that Example 2 provided a simple process and higher sensitivity.

Further, as shown in FIG. 4, both of Examples 1 and 2 exhibited a higher detection sensitivity than that in Comparative 1 in detecting W. The results show that the contamination control method of the invention allows simple recognition of the contamination status and higher sensitivity in detecting W.

It should be noted that, when the results for Mo and the results for W are compared, Comparative 1 shows approximately twice higher detection sensitivity ratio for Mo than the detection sensitivity ratio for Mo. On the other hand, Examples 1, 2 exhibited approximately three times higher detection sensitivity ratio for W than the detection sensitivity ratio for Mo. According to the comparison, it is found that the contamination control method of the invention can enhance, especially, the detection sensitivity for W.

Example 3

The same n-type silicon wafer having 300 mm diameter as that in the above Example 1 was prepared as a monitor wafer and the same epitaxial growth apparatus was used. Then, various treatments were applied according to the following conditions to produce monitor wafers in which metal contamination was emphasized.

Metal-contamination-emphasized monitor wafer(s) was produced through a cleaning step, coating step, wafer loading step, heat-treatment repetition step, and wafer unloading step. The repetition number of the heat-treatment steps in the heat-treatment repetition step was five. The treatment conditions in the cleaning step were HCL gas atmosphere, heat treatment temperature of 1120 degrees C., and treatment time of 75 seconds. The treatment conditions in the heat-treatment step were trichlorosilane gas atmosphere, heat treatment temperature of 1120 degrees C., and treatment time of 30 seconds. The treatment conditions in the heat-treatment step were hydrogen gas atmosphere, heat treatment temperature of 1120 degrees C., and treatment time of 270 seconds. The treatment conditions in the second heat-treatment step were HCL gas and hydrogen gas atmosphere, heat treatment temperature of 1150 degrees C., treatment time of 15 seconds, and HCL supply flow rate of 0.75 slm.

Example 4

Except that the coating step was not conducted, metal-contamination-emphasized monitor wafer(s) was produced in the same manner as in the above Example 3.

Wafer Contamination Evaluation 2

Figure 5:
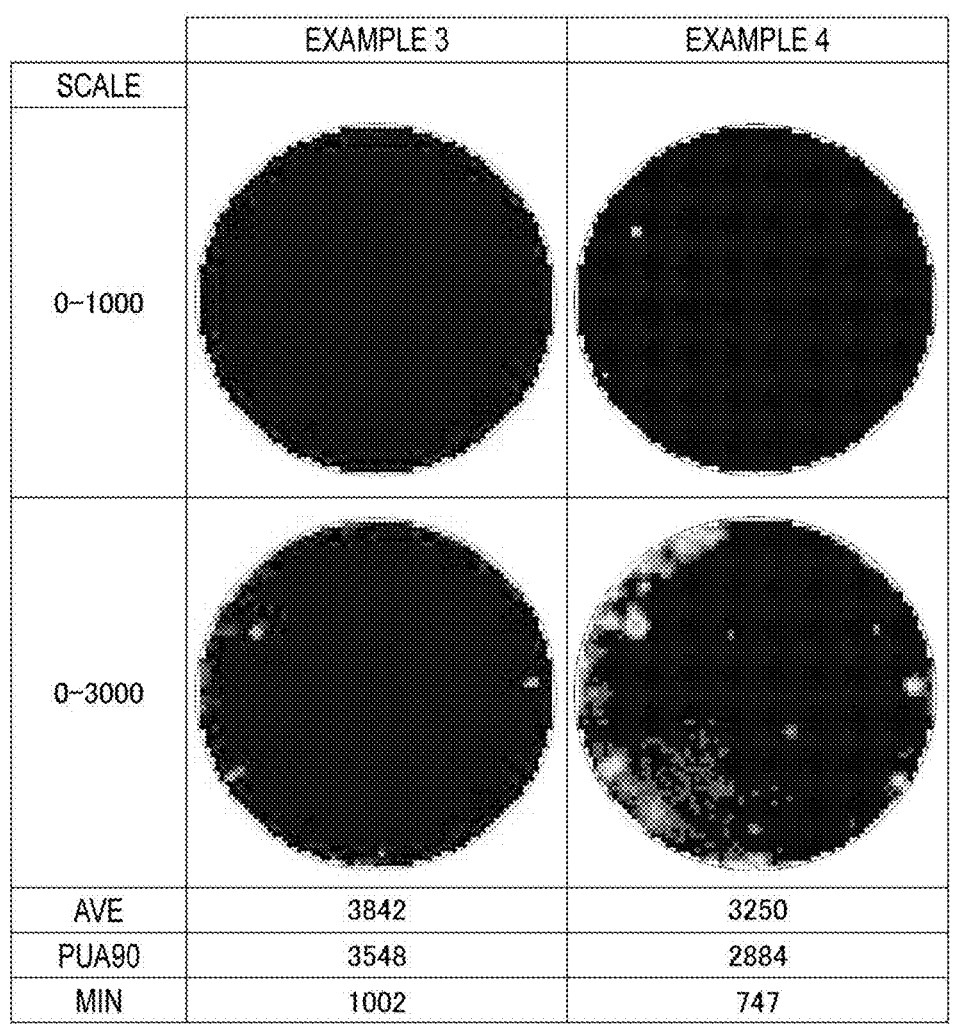
FIG. 5 shows results of lifetime analysis in Examples 3 and 4.

Recombination lifetimes of the monitor wafers having experienced the various treatments in Examples 3 and 4 were measured using μ-PCD method. FIG. 5 shows the results.

As is clear from FIG. 5, in Example 4 where no coating step was conducted and thus no polysilicon film was formed on the surface of the susceptor, it is found that the decrease in lifetime occurred in a spotted manner. It is speculated that the spotted decrease in lifetime is caused by the metal contamination derived from the susceptor. On the other hand, in Example 3, in which the coating step was conducted to form a polysilicon film on the surface of the susceptor, the above influence of the metal contamination was alleviated as compared to Example 4. According to the above results, it is found that the coating step allows clearer evaluation without being influenced by the metal contamination derived from the susceptor.

What is claimed is:

1. A contamination control method of a vapor deposition apparatus, comprising:

loading a monitor wafer into an interior of a chamber of the vapor deposition apparatus;

consecutively repeating a heat treatment for thermally treating the monitor wafer loaded into the interior of the chamber for a predetermined number of times without unloading the monitor wafer from the chamber;

unloading the monitor wafer after experiencing the repetition of the heat treatment from the interior of the chamber; and evaluating a metal-contamination degree of the monitor wafer unloaded out of the chamber, wherein the heat treatment comprises:

a first heat-treatment, in which a hydrogen-chloride-containing gas is not fed into the interior of the chamber but a hydrogen-containing gas is fed into the chamber to thermally treat the monitor wafer in an atmosphere of the hydrogen-containing gas to reduce a vaporized amount of metal adhered on a surface of the monitor wafer and to remove a natural oxide film present on the surface of the monitor wafer; and a second heat-treatment, in which the hydrogen-chloride-containing gas and the hydrogen-containing gas are fed into the interior of the chamber to thermally treat the monitor wafer in an atmosphere of the hydrogen-chloride-containing gas and the hydrogen-containing gas to activate the surface of the monitor wafer.

2. The contamination control method of a vapor deposition apparatus according to claim 1, wherein a heat treatment temperature of the second heat-treatment is in a range of a heat treatment temperature in the first heat-treatment ±100 degrees C.

3. The contamination control method of a vapor deposition apparatus according to claim 1, wherein a treatment time of the second heat treatment is in a range from 1 to 200 seconds.

4. The contamination control method of a vapor deposition apparatus according to claim 1, wherein a supply flow rate of the hydrogen-chloride-containing gas in the second heat-treatment is in a range from 0.1 slm to 5.0 slm.

5. The contamination control method of a vapor deposition apparatus according to claim 1, wherein a heat treatment temperature in the first heat-treatment is in a range from 900 to 1200 degrees C.

6. The contamination control method of a vapor deposition apparatus according to claim 1, wherein a repetition number of the repetition of the heat-treatment steps is in a range from 2 to 20.

7. The contamination control method of a vapor deposition apparatus according to claim 1, wherein prior to loading the monitor wafer into the chamber, a vapor-phase etching is applied to the interior of the chamber using the hydrogen-chloride-containing gas to clean the interior of the chamber.

8. The contamination control method of a vapor deposition apparatus according to claim 7, further comprising:

after cleaning the interior of the chamber, raising a temperature of a susceptor inside the chamber to a predetermined temperature range, and circulating a silane-containing gas in the chamber to form a polysilicon film on the surface of the susceptor.

9. The contamination control method of a vapor deposition apparatus according to claim 1, wherein the evaluation of the wafer contamination is performed based on a metal concentration measurement by a chemical analysis and/or a lifetime measurement.

10. The contamination control method of a vapor deposition apparatus according to claim 9, wherein the chemical analysis is performed using an induction coupled plasma mass spectrometry.

11. The contamination control method of a vapor deposition apparatus according to claim 9, wherein the chemical analysis is performed using a vapor-phase decomposition.

12. A production method of an epitaxial silicon wafer, comprising:

producing an epitaxial silicon wafer using a vapor deposition apparatus that is controlled by the contamination control method according to claim 1.

* * * * *